United States Patent [19]
Hilston et al.

[11] Patent Number: 5,951,507
[45] Date of Patent: Sep. 14, 1999

[54] PROCESS FOR MANUFACTURING TAPE PRODUCTS

[75] Inventors: Michael D. Hilston, Painesville; Rochael Collins Swavey, Mentor; Robert Wanska, Thompson; Karen Spilizewski, Euclid; Theresa Carte', Wickliffe; Richard Katona, Mentor, all of Ohio

[73] Assignee: Avery Dennison Corporation, Pasadena, Calif.

[21] Appl. No.: 09/094,767

[22] Filed: Jun. 15, 1998

Related U.S. Application Data

[60] Provisional application No. 60/048,926, Jun. 16, 1997.

[51] Int. Cl.$^6$ ..................................................... A61F 13/00
[52] U.S. Cl. .................................. 602/52; 602/41; 602/46
[58] Field of Search .................................. 602/52, 41, 46; 128/156

[56] References Cited

U.S. PATENT DOCUMENTS

| | | | |
|---|---|---|---|
| 3,407,166 | 10/1968 | Kuceski et al. | 260/32.6 |
| 3,972,328 | 8/1976 | Chen | 128/156 |
| 4,341,209 | 7/1982 | Schaar | 128/156 |
| 4,733,659 | 3/1988 | Edenbaum et al. | 128/156 |
| 4,780,168 | 10/1988 | Beisang et al. | 156/256 |
| 4,981,755 | 1/1991 | Cascino | 428/317.3 |
| 5,322,695 | 6/1994 | Shah et al. | 424/448 |
| 5,633,070 | 5/1997 | Murayama et al. | 428/194 |

FOREIGN PATENT DOCUMENTS

| | | |
|---|---|---|
| 0 676 183 A1 | 10/1995 | European Pat. Off. . |
| 289 222 A5 | 11/1989 | Germany . |
| 4153234 | 10/1990 | Japan . |
| 4198289 | 11/1990 | Japan . |
| 2 191 403 | 12/1987 | United Kingdom . |

OTHER PUBLICATIONS

O'Brien, Joseph, W.H. Whittington, and Glen Chalfant. "New Glutarate Polyester Plasticizers for PVC." *Plastics Compounding*, May/Jun. 1981, pp. 62–67.

*Primary Examiner*—Richard J. Apley
*Assistant Examiner*—Kelvin Hart
*Attorney, Agent, or Firm*—Renner, Kenner Greive, Bobak Taylor & Weber

[57] ABSTRACT

A one stage process for the manufacture of a plastisol film or foam tape laminate comprises providing a continuous liner; forming a release layer along the length of one side of the liner; depositing an adhesive onto the release layer; casting a liquid plastisol formulation onto the adhesive; fusing, and in the case of a foam tape expanding, the plastisol formulation to form a thermoplastic layer on the adhesive; and, winding the resulting tape laminate onto rolls.

60 Claims, 3 Drawing Sheets

PROCESS FOR MANUFACTURING TAPE PRODUCTS

This application claims priority from United States Provisional Application No. 60/048,926, filed Jun. 16, 1997.

TECHNICAL FIELD

The present invention is directed to a process for manufacturing tape products. More particularly, it is directed to a process for manufacturing an adhesive tape comprising a plastisol film or foam and an adhesive, on a release liner.

BACKGROUND OF THE INVENTION

It has been the practice in the art to cast a plastisol film or foam suitable for use as a tape product, such as a bandage or wound dressing, on a casting sheet in a first stage on one apparatus, and then deliver the laminate to a second apparatus in roll form. The casting sheet is conventionally a siliconized paper about 60 inches wide, and several thousand yards long, impregnated with clay or some other saturant, to provide a smooth surface for the cast.

On the second apparatus, the roll of the film or foam/casting sheet laminate is mounted for contacting with a liner (such as a kraft paper on the order of about 60 pounds), which liner is first coated on one side with a release layer, such as a silicone compound, and then coated with an adhesive on top of the silicone. The film or foam is then laminated in the second stage to the adhesive layer, such that the film or foam is interposed between its casting sheet, or carrier, on one side, and the adhesive layer of the new adhesive coated liner on the other side. The casting sheet, or carrier, is then stripped off of the laminate, and is discarded.

If the tape product is to be used as a bandage or wound dressing, the rolled sheet is perforated (such as being rolled with pins) and then is cut to size, in one application on the order of 3¼ inches wide, although the width could vary. The length of the bandage, is thereafter cut from the width of the roll, in a third stage. The narrow laminate is conventionally wound in large rolls, for delivery to a third apparatus.

In a third stage, the heavy liner is stripped off the narrow laminate. The adhesive sticks to the film or foam, but not the liner. In the case of a bandage, an adsorbant pad is applied to the adhesive, and a new about 40 to about 50 pound liner, comprising two overlapping pieces that form the "pull tab", is laminated. The new laminate is then passed to a cutter, or a die.

In one embodiment, the plastisol foam comprises foamed polyvinyl chloride, or PVC foam. PVC foam is conventionally cast at the relatively high temperature of about 300° to about 400° F., requiring a dense casting surface with easy release. Otherwise, the resulting PVC foam will not form a flat, glossy sheet as desired, as water vapor or bubbles adsorbed on the casting sheet will be taken up in the foam. Also, if a dense casting sheet is not utilized, an easy release will not be effected in the stripping process in the third stage.

In the conventional process, a rate limiting step is stripping off the heavy casting sheet during the second stage, at the point thatAthe film or foam is laminated to the adhesive coated release liner. Further, the heavy, treated casting sheet is normally discarded. It is therefore desirable to bypass the rate limiting procedure. It is further desirable to economize by avoiding the use of the heavy, extra casting sheet, such that the cost of both its purchase in the first instance, and its disposal after use, are avoided.

A further disadvantage to the conventional process is that it is necessary, during the second stage, to splice both the liner and the film or foam, when each reaches the end of the rolls on the apparatus. The spliced section passes through to the third stage and into the finished product. These spliced products must be culled out of the product before packaging and/or delivery to the customer. This culling process causes additional wastage and the slowing of run speeds, resulting in inefficiencies in the process.

Another disadvantage in the conventional process, that is, utilizing a preformed film or foam on a casting sheet, is the requirement that the adhesion of the film or foam to the adhesive coated release liner be more tenacious than the adhesion to the casting sheet, so that the casting sheet can be stripped off without delaminating the film or foam from the liner. This balance is difficult to achieve. Also, too high an adhesion to the liner will make conversion of the tape laminate to, for example, a bandage type product more difficult, as the release liner must then then be stripped from the tape.

SUMMARY OF THE INVENTION

It is therefore an object of the present invention to provide a process for casting a plastisol film or foam directly onto an adhesive coated release liner.

It is a further object of the present invention to avoid the use and cost of a heavy casting sheet that is discarded prior to sizing the width of the tape product.

It is a further object of the present invention to provide a continuous plastisol film or foam tape and a process for producing it, that does not contain sections of spliced film or foam material.

The present invention therefore provides a process for the manufacture of a tape comprising providing a continuous liner having a release layer; depositing an adhesive onto the release layer; casting a liquid plastisol formulation onto the adhesive; and, fusing the plastisol formulation to form a thermoplastic layer on the adhesive.

In one embodiment, the present invention provides a process for the manufacture of a plastisol foam tape comprising providing a continuous liner having a release layer; depositing an adhesive onto the release layer; casting a foamable liquid plastisol formulation onto the adhesive; and, fusing and expanding the foamable plastisol formulation to form a plastisol foam on the adhesive.

Preferably, the adhesive is dried prior to casting the liquid plastisol formulation, which in one embodiment of the invention comprises polyvinyl chloride and plasticizer.

In one embodiment, the present invention further includes cutting the tape substantially parallel to its long axis to a selected width, and winding the tape onto rolls.

The present invention further provides a one stage process for the manufacture of a tape laminate comprising providing a continuous liner; forming a release layer along the length of one side of the liner; depositing an adhesive onto the release layer; casting a liquid plastisol formulation onto the adhesive; fusing the plastisol formulation to form a thermoplastic layer on the adhesive; and, winding the resulting tape laminate onto rolls. The present invention further provides the tape product of the process.

The present invention further provides a one stage process for the manufacture of a plastisol foam tape laminate comprising providing a continuous liner; forming a release layer along the length of one side of the liner; depositing an adhesive onto the release layer; casting a foamable liquid plastisol formulation onto the adhesive; fusing and expanding the foamable plastisol formulation to form a plastisol foam on the adhesive; and, winding the foam tape laminate onto rolls. The present invention further provides the foam tape product of the process.

PREFERRED EMBODIMENTS OF THE INVENTION

Figure 1:
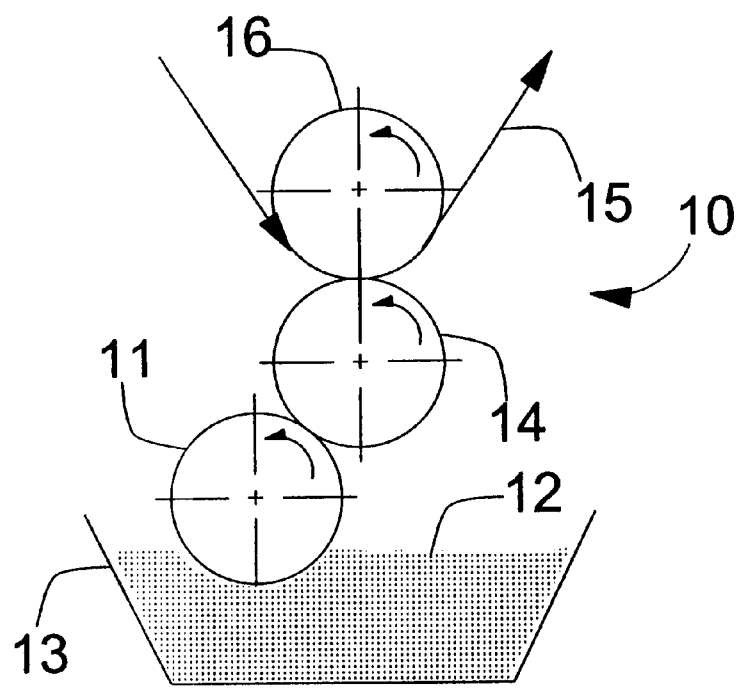
FIG. 1 is a schematic representation of a three roll reverse coating system.

The present invention is directed to a process for manufacturing a continuous plastisol film or foam adhesive tape laminate in a single operation. The present invention avoids having to cast the film or foam in an operation separate from the formation of the laminate of the film or foam with the adhesive coated release liner.

Optimally, the entire laminate is prepared in one continuous operation, including the formation of the release layer on the liner, the deposition and drying of the adhesive, and the casting (depositing), and if applicable, the foaming of the plastisol formulation on the adhesive layer. It is within the scope of the invention, however, to separately form the liner/release/adhesive laminate, and thereafter cast the plastisol formulation onto exposed adhesive, optionally in a separate stage, as the advantages of the present invention derive in part from avoiding the use of a heavy, discardable casting sheet for the film or foam. The invention includes the discovery that a high quality film or foam can be cast, fused and (in the case of a foam) heat expanded directly on an adhesive without damage to the adhesive's properties, or the fusing of the adhesive with the underlying release layer.

In one embodiment of the invention, a heavy weight, clay coated kraft paper, on the order of about 62 pounds to about 78 pounds, is provided as a continuous liner. A release layer is formed by applying a conventional silicone release compound onto the liner and curing. An adhesive is deposited onto the silicone release layer, such as by casting a liquid solution of the adhesive and then drying.

A liquid, foamable plastisol formulation is then cast (deposited) onto the dried adhesive, and subjected to heat sufficient to fuse and then expand the plastisol formulation into a foam. For a PVC plastisol, the temperature range for expanding the foam is generally on the order of about 300° to about 400° F.

Surprisingly, we have demonstrated that it is possible to cast a foamable plastisol onto an adhesive surface, and still get a good quality foam, comparable to or improved over plastisol foams prepared by casting onto a conventional casting sheet. Further, it was unpredictable that the adhesive would still have adhesive properties once it had the plastisol formulation (which includes a plasticizer) applied to it and went through an oven at the high foam expanding temperatures required to fuse and expand PVC plastisols into foam. The adhesive, rather than fusing to the silicone compound upon exposure to the high temperature as was expected, releases from the silicone when pulled, but retains sufficient adhering properties for use in the tape product.

Further, we have found that when the plastisol is cast and fused in place on top of the adhesive, the bond between the adhesive and the resulting thermoplastic layer is greater than when the adhesive is laminated to the thermoplastic. One test for adhesive tenacity to the film or foam is to contact the adhesive on the film or foam to itself and pull the adhered sections apart, to determine whether any adhesive comes off. Adhesive pickoff is a critical test for bandages, as it is undesirable for the adhesive to come off of the bandage onto the skin of the user.

For the liner paper, a dense surface is needed. Even though a silicone and an adhesive is layered on the paper, if there is porosity in the paper, the film or foam that is cast onto it will have defects, such as pinholes, voids, and bubbles, resulting from moisture coming out of the paper at high temperature and evaporating, and/or geometric variations in the surface of the paper. A suitable weight paper is about 40 pounds to about 100 pounds, preferably about 62 pounds to about 78 pounds. A light weight release liner will tend to curl from the wet plastisol. Heavier weight liners approximate the casting paper which is avoided by the present invention. The liner papers used according to the present invention need not be stripped and replaced prior to perforation of the film or foam and conversion of the sized product roll to the thin, overlapping "pull-tab" lined product (such as for a bandage).

The surface of the paper is preferably clay coated, or coated with another conventional saturant. Suitable papers include, but are not limited to, 58, 63 and 78 pound clay coated, supercalendered kraft paper, available from Boise Cascade Corporation (Portland, Oreg.). Other suitable liners include pre-siliconized release coated Multithane or Ultra-Matte liners from Arjo Wiggins, and lacquered liners from Boise Cascade or Avery Dennison Release Coated Materials Division (Mentor, Ohio).

Suitable release compositions for use in the present invention include conventional silicone release compounds, including platinum or rhodium catalyst cured silicone and radiation cured release coatings. As stated above, the release layer can be applied in the same operation as the casting of the plastisol layer, or can alternatively be precoated on the liner. The silicone release compound is preferably an easy release system, for use in tape products. Suitable silicone release compositions include, but are not limited to vinyl-substituted polydimethylsiloxane resins such as GE SS4331 or GE 5000 from GE Plastics, and Syl-Off resin systems from Dow.

The adhesive useful in the present invention is a pressure sensitive adhesive, releasable from the underlying release composition. The adhesive should not be adversely affected by the plastisol formulation. Suitable adhesives include those that are acrylic based adhesives, preferably, those that are not tackified, and most preferably having high crosslinker levels.

The adhesive is preferably applied to the release layer as a solution of the acrylic composition. In one embodiment, the acrylic adhesive is applied in a toluene and/or heptane solvent or emulsion, and the solvent or carrier liquid is dried off by heating, at about 120° to about 240° F., preferably about 140° to about 180° F. In another embodiment, a vinyl pyraolidone polymer in a hexane/toluene solvent is utilized, having a crosslinker. The thickness of the dried adhesive layer varies with the application for which it is intended. For skin bandages, the adhesive layer is generally on the order of about 1.5 to about 2.5 mils thick.

When the tape product is a bandage, the adhesive composition is a biocompatible pressure sensitive adhesive. Preferably it is a polyvinyl ester-based acrylic adhesive. The adhesive may have relatively low aggressiveness, but should have sufficient adhesion to skin when used with the film or foam of the present invention. The adhesive may be the same as those in conventional bandages, at coating weights from about 10 g/m$^2$ to about 250 g/m$^2$, preferably from about 25 g/m$^2$ to about 75 g/m$^2$.

The coating conditions for both the release layer and the adhesive are conventional in the industry. As is the case with the release layer, the adhesive layer can be applied in the same operation as the casting of the plastisol layer, or can alternatively by precoated on the release liner. The adhesive can be applied in a uniform coat, or in a pattern appropriate for the end product.

It should be noted that the adhesive is dried at high temperature in proximity to the silicone release compound. Further, the silicone release compound and the adhesive are "heat aged" in contact with each other while making the tape product, as the plastisol formulation is expanded to produce the foam in one embodiment, at about 300° to about 400° F. If the adhesive and the release compound do not have a very easy release characteristic with respect to each other, the two compositions will weld, and will not be able to be separated when the laminate is stripped to replace the intermediate weight casting liner with the light weight paper liner of the final product.

In a test to determine release properties, the silicone release composition is applied to the liner paper and is cured. A sheet having the adhesive on it is then laminated to the silicone. After subjecting the laminate to the heat aging conditions, the force it takes to peel them apart is measured on an Instron tester.

A steel plate (Keil plate) is placed on the laminate at 0.25 psi pressure and placed in an oven at 158° F. for 20 hours. The laminate is then pulled apart at 300 inches per minute at a 90° peel angle.

The release force should not be too low, and should preferably be greater than 50 grams/2 inches because during the production process, the laminate normally passes over and under rollers. The aggressive adhesive side contacts rollers, but must stay on the silicone release compound and not transfer onto the roller. An unacceptable force is greater than 500 grams/2 inches of sample width, since it is undesirable for subsequent processing, due to the tendency of the film, foam or paper to tear at high release forces. According to the present invention, a peel force of 200–225 grams/2 inches is achieved, as compared to a control formulation providing 350–400 grams/2 inch tape peel force. A peel force up to about 400 grams/2 inches is acceptable, but it is preferably lower.

The plastisol formulation which is cast onto the adhesive layer of the adhesive/release/liner laminate comprises a resin, a plasticizer, and in the case of the foam a blowing agent, and optionally an activator/stabilizer, a viscosity depressant, pigment, filler and defoamer. The plastisol preferably contains a PVC resin.

The plastisol formulation preferably contains about 100 to about 120 parts by weight plasticizer per 100 parts resin when a foamable resin formulation is desired, together with about 0.5 to about 2 parts blowing agent. A foamable plastisol resin dispersion may comprise a foamable PVC resin, and optionally up to about 40% of the total resin of a blending resin. When a film, rather than a foam is to be manufactured, the plastisol formulation preferably contains about 30 to about 100 parts by weight plasticizer per 100 parts resin, and the blowing agent is omitted.

The plastisol formulation is applied to the adhesive layer of the adhesive/release/liner laminate in a solventless, solution or slurry/dispersion form. Techniques conventional in the industry for applying plastisol formulations to a substrate can be used, such as roll coating, knife over roll coating, and extrusion or slot coating.

A representation of three roll reverse coating 10 is shown in FIG. 1, in which a fountain roll 11 carries the plastisol formulation 12 solution or dispersion from a reservoir 13 to an application roll 14, which then accurately applies the plastisol formulation 12 onto the adhesive layer of the laminate 15, being carried by the backing roll 16. The thickness of the liquid plastisol coating is controlled by the speed of the application roll 14 as well as the gap between the fountain roll 11 and application roll 14 and the gap between the application roll 14 and backing roll 16, considering the thickness of the laminate 15 onto which the plastisol is being applied. This coating method is versatile and accurate, and handles a wide range of viscosities of the plastisol formulation. It can accommodate uneven web surfaces, to yield a uniform plastisol film thickness.

Figure 2:
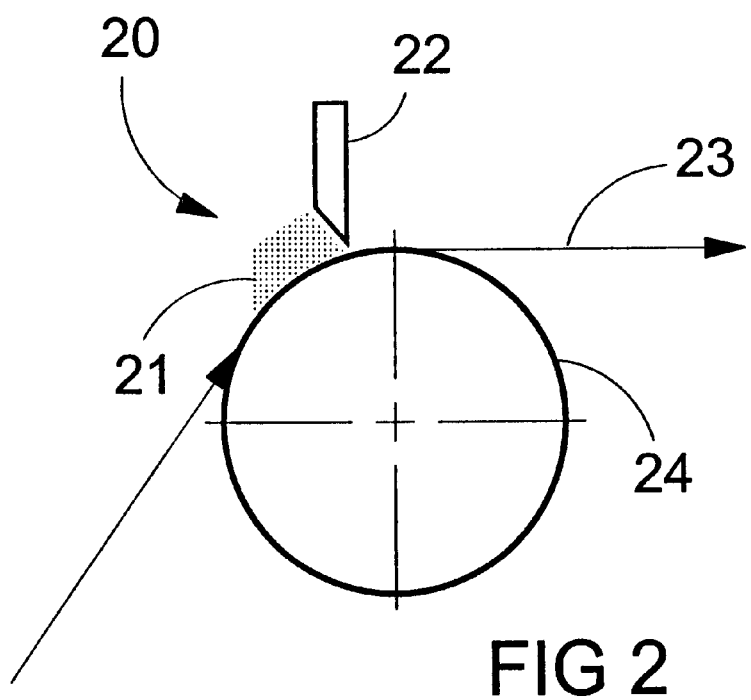
FIG. 2 is a schematic representation of a knife over roll coating system.

An alternative application technique is the knife over roll method 20, represented in FIG. 2. In this high shear method, the plastisol formulation liquid 21 is extruded from a passage formed by a rigid and stationary knife 22, under which is passing the adhesive/release/liner laminate 23 supported by a hard backup roll 24. This technique accommodates a variety of feed systems conventional in the art, such as roller feed, hopper feed, and die feed. This method also accommodates a wide viscosity range of the plastisol formulation 21, and is simple to operate. The coating thickness of the plastisol coating is effected by the gap between the knife 22 and the laminate 23 carried on the backup roll 24 (the coating being about ½ the thickness of the gap), by blade thickness, viscosity (increasing lowers weight of plastisol applied), web speed (increasing lowers weight of plastisol applied), and plastisol fluid surface tension (increasing the surface tension increases the weight applied).

Figure 3:
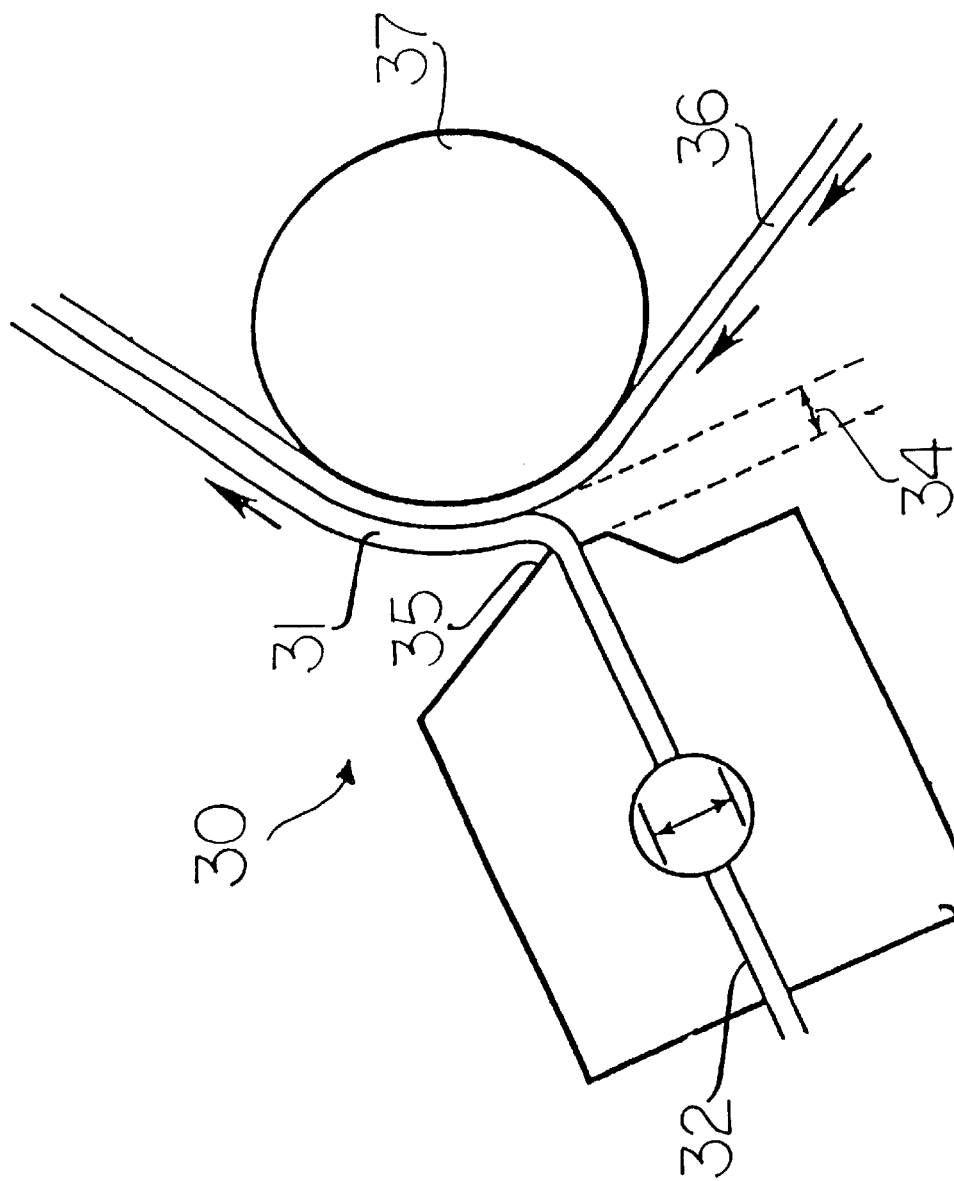
FIG. 3 is a schematic representation of a slot coating system.

A third method for applying the plastisol to the adhesive/release/liner laminate is by slot coating 30, represented in FIG. 3. This technique is very accurate, but is most difficult to control. The plastisol formulation fluid 31 is extruded through a slot 32 in a die body 33, into a coating gap 34 between the die outlet 35 and the laminate 36, being carried on a backing roll 37. Thickness of the coating is controlled by the thickness of the gap, flow rate, density and temperature of the fluid, the rheology curve (shear/viscosity) and the thixotropy of the fluid (viscosity decreasing with increased shear). Other variables include the diameter of the backing roll 37, the backing roll hardness, and the web 36 line speed.

The thickness of the plastisol formulation which is applied depends upon the application for which it is intended. For skin bandages, generally a thickness of about 3 to about 20 mils is desired. In one embodiment, it is preferred that the thickness of the liquid plastisol coating be about 10 mils.

The plastisol liquid is then subjected to heat, sufficient to fuse the resin, and in the case of a foam, to expand the foam, by activation of the blowing agent in the formulation. The blowing agent may be activated either during or after extrusion of the plastisol onto the laminate. Activation is by means conventional in the art, such as by heating in an oven.

Expansion of the foam generally results in the thickness of the plastisol foam being about twice the thickness of the applied liquid coating. For example, the expansion of a 10 mil liquid plastisol coating can result in a foam of about 20 to about 22 mils thick. The amount of expansion is controlled by variables such as dwell time, temperature, and the amount and type of blowing agent.

Figure 4:
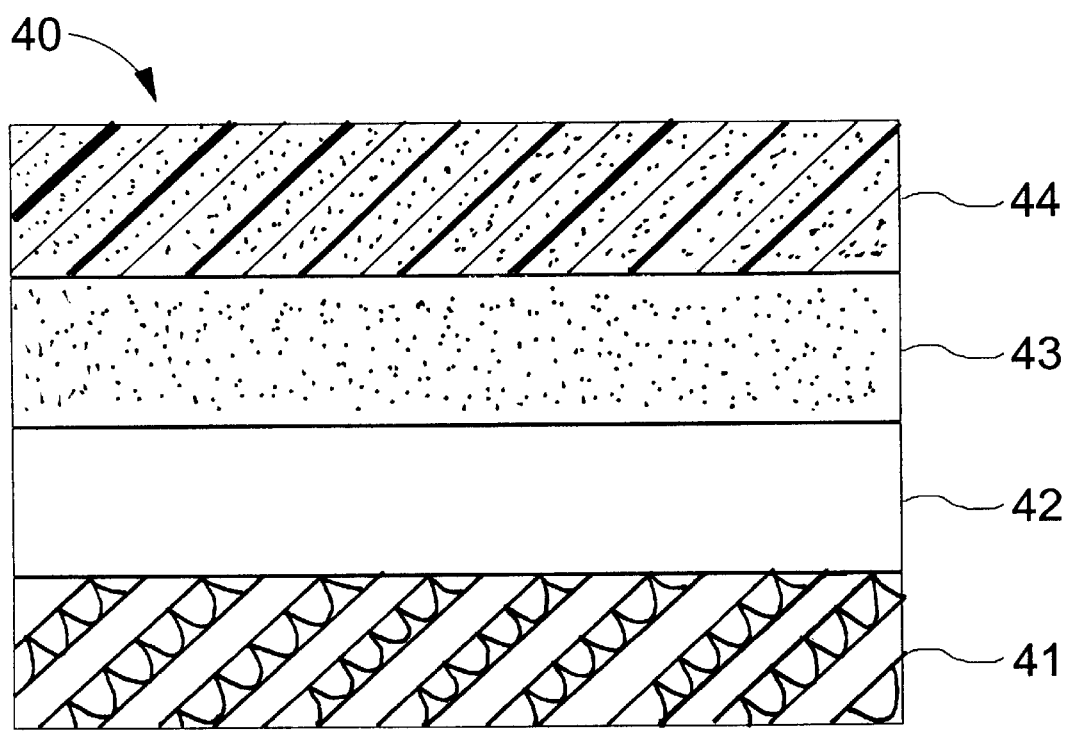
FIG. 4 is a cross sectional view of a foam tape laminate produced according to the process of the present invention.

A representation of a foam tape 40 produced according to the present invention is shown in FIG. 4. The liner backing 41 carries the release layer 42, onto which is disposed the adhesive 43, over which is coated the foam 44. If the foam 44 is to be used as a skin bandage, it is rendered more permeable to air by perforation, such as by passing the foam carrying laminate in contact with a roller carrying pins for perforating the foam.

EXAMPLES OF THE INVENTION

Polyvinyl chloride (PVC) plastisol formulations prepared according to the examples set forth below were cast on an adhesive coated release liner and tested for acceptability with regard to drape, conformability, and strength characteristics.

Example 1

A plastisol formulation set forth below was prepared and expanded to produce a foam tape, suitable for use in the process of the present invention.

| Components: | phr |
| --- | --- |
| PVC dispersion resin | 100 |
| Polyester plasticizer | 120 |
| Activator/stabilizer | 3 |
| Azodicarbonamide blowing agent | 1.2 |
| Defoamer | 0.25 |
| Aromatic hydrocarbon solvent | 16 |
| mineral spirits solvent | 7 |
| Flesh colored pigments | 2.1 |

This formulation yielded a soft foam with a tacky texture.

Example 2

For the reduction of solvent in the plastisol, a 30 micron PVC blending resin (VC-260SS) was added to the formulation and the amount of the 1 micron diameter foamable resin (Geon 180X7) was reduced. By the addition of the blending resin, the solvent concentration was reduced from 23 phr to 6 phr without an increase in the final viscosity.

| Components: | phr |
| --- | --- |
| PVC dispersion resin | 60 |
| PVC blending resin | 40 |
| Polyester plasticizer | 120 |
| Activator/stabilizer | 3 |
| Azodicarbonamide blowing agent | 1.2 |
| Defoamer | 0.25 |
| Odorless mineral spirits solvent | 6 |
| Flesh colored pigments | 1.1 |

The formulation of example 2 yielded a soft foam with nice drape. Physical evaluation of 18 mil foam gave a density of 33 lb./cu.ft., tensile strength of 4.7 lb./in. "down web" or in the machine direction (MD), and elongation of 272% (MD).

Example 3

The plasticizer of Examples 1 and 2 was replaced with a benzyl phthalate plasticizer (Santicizer 278) which is considered a migration resistant high monomeric/low polymeric plasticizer (MW=455). The resulting formulation had the following components:

| Components: | phr |
| --- | --- |
| PVC dispersion resin | 60 |
| PVC blending resin | 40 |
| Benzyl phthalate plasticizer | 125 |
| Activator/stabilizer | 3 |
| Azodicarbonamide blowing agent | 1.5 |
| Defoamer | 0.25 |
| Odorless mineral spirits solvent | 2 |
| Flesh colored pigments | 1.1 |

The formulation of example 3 yielded a stiffer and stronger foam than the formulation of example 2. Physical measurements found the density to be 29 lbs./cu.ft., tensile strength 6.5 lbs./in. (MD), and elongation 240% (MD). Adhesive aging studies up to 4 weeks were investigated on laminated samples with no adhesive failure, and only a 39% drop from initial peel value when aged at 158° F.

Example 4

A phosphate ester plasticizer was added to the benzyl phthalate formulation to soften the foam, and additionally, all solvent was able to be removed. The formulation had the following components:

| Components: | phr |
| --- | --- |
| PVC resin | 60 |
| PVC blending resin | 40 |
| Benzyl phthalate plasticizer | 100 |
| Phosphate ester plasticizer | 15 |
| Activator/stabilizer | 3 |
| Azodicarbonamide blowing agent | 1.5 |
| Defoamer | 0.25 |
| Solvent | 0 |
| Flesh colored pigments | 1.1 |

The formulation of Example 4 yielded a slightly softer foam than Example 3, with a glossy surface. Physical measurements found the density to be 37 lbs./cu.ft., tensile 5.8 lbs./in. (MD), and elongation 226% (MD). Initial peel studies showed less favorable lamination of the adhesive to the glossy surface of the foam, but aging up to 8 weeks did not display adhesive failure (64% drop from initial peel value when aged at 158° F.).

Example 5

Alternate polymeric plasticizers were also investigated in the plastisol formulation. Polymeric plasticizers resisted plasticizer migration into the acrylic adhesive of the laminate. A polyester adipate plasticizer was therefore substituted in the plastisol formulation. The plastisol had the following formulation:

| Components: | phr |
| --- | --- |
| PVC dispersion resin | 100 |
| Polyester adipate plasticizer | 120 |
| Activator/stabilizer | 3 |
| Azodicarbonamide blowing agent | 1.2 |
| Defoamer | 0.25 |
| Odorless mineral spirits solvent | 4 |
| Flesh colored pigments | 1.1 |

The formulation of Example 5 produced a very soft foam which tore easily. Density was low, 17 lbs./cu.ft., and a tensile strength of 2.3 lb./in. and elongation of 183% was exhibited.

Example 6

The above formulation using a polyester adipate plasticizer was improved upon by changing the molecular weight of the plasticizer and by adjusting its level in the formulation to produce a stronger foam. The blowing agent level was also reduced to increase the density. The plastisol formulation was as follows:

| Components: | phr |
| --- | --- |
| PVC dispersion resin | 100 |
| Polyester adipate plasticizer | 100 |
| Activator/stabilizer | 3 |
| Azodicarbonamide blowing agent | 0.8 |
| Defoamer | 0.25 |
| Odorless mineral spirits solvent | 3 |
| Flesh colored pigments | 1.1 |

The formulation of Example 6 produced a foam with nice drape. The density was measured as 21 lb./cu.ft. and a tensile strength of 6.2 lb./in. and 285% elongation was exhibited for a 24 mil foam. A 20 mil foam should therefore result in a tensile strength of about 5.5 lb./in. and elongation of about 280%.

Example 7

A polyvinyl chloride film adhesive tape was produced according to the process of the present invention, by omitting the foaming agent and the foam expansion step, using the following formulation.

| Components: | phr |
| --- | --- |
| PVC dispersion resin | 100 |
| Polyester plasticizer | 30 |
| Stabilizer | 3 |
| Defoamer | 0.25 |
| Aromatic solvent | 35 |
| Aliphatic solvent | 12 |
| Epoxidized Soybean Oil | 4 |

We have found that when the plastisol formulation is cast on the adhesive/silicone/liner laminate, a better quality film or foam is achieved compared to one cast on silicone/liner alone, as the adhesive helps to further smooth and densify the surface of substrate.

The PVC tape manufactured according to the process of the present invention has the following characteristics: Softness, conformability and drape; tensile strength; resistance to tearing; air permeability (transmissibility via perforation); elasticity (percent elongation); processability; cutability (die cutable); and particularly when used for bandages or wound dressings, medical safety (no harmful components); stability over time; resistance to sterilization, steam, and radiation.

The process of the present invention is useful for preparing self-adhesive tape products such as bandages, wound dressings, medical tapes, such as for adhering an electromedical device (e.g., a diagnostic device), mounting tapes, tapes for industrial uses, labels, and the like.

The present invention therefore is demonstrated as providing a process for casting a plastisol derived film or foam tape directly onto an adhesive coated release liner, thereby avoiding the use and cost of a heavy casting sheet that would otherwise be discarded prior to sizing the width of the tape product.

The continuous plastisol film or foam tape produced by the process of the present invention does not contain sections of spliced film or foam material. According to the prior art, double splices were needed, one in the tape and one in the liner, each time a new roll was put on the apparatus. According to the present invention, only one splice is needed, at the end of the roll of the liner sheet. When the sized tape roll is further processed to replace the liner with the lightweight paper liner, the liner splice goes into the scrap roll.

According to the process of the present invention, a higher quality film or foam tape is achieved by casting the plastisol formulation directly onto the adhesive coated release liner. Improved anchorage of the thermoplastic film or foam layer to the adhesive in the tape product is also obtained through the process of the present invention.

The tape product obtained by the process of the present invention is useful as skin bandages, and therefore the plastisol dispersion used may contain flesh colored pigments, or pigments producing other colors, including but not limited to "designer" colors and fluorescent colors.

Thus, the objects of the invention are accomplished by the present invention, which is not limited to specific embodiments described above, but which includes variations modifications and equivalent embodiments defined by the following claims.

We claim:

1. A process for the manufacture of a plastisol foam tape comprising:
   providing a continuous liner having a release layer;
   depositing an adhesive onto the release layer;
   casting a foamable liquid plastisol formulation onto the adhesive, wherein the adhesive is dried prior to casting the liquid plastisol formulation; and,
   fusing and expanding the foamable plastisol formulation to form a plastisol foam on the adhesive.

2. The process as in claim 1 including applying the release layer to the liner prior to the depositing of the adhesive.

3. The process as in claim 1 wherein the plastisol comprises polyvinyl chloride, plasticizer and a blowing agent.

4. The process as in claim 3 wherein the plastisol additionally comprises at least one of a polyvinyl chloride blending resin, an activator, a stabilizer, a viscosity depressant, a defoamer, a solvent, a filler and a pigment.

5. The process as in claim 3 wherein the plastisol formulation is expanded by heating the formulation at about 300° to about 400° F.

6. The process as in claim 1 further including cutting the tape substantially parallel to its long axis to a selected width.

7. The process as in claim 1 further including winding the tape onto rolls.

8. The process as in claim 1 wherein the adhesive comprises an acrylic adhesive.

9. The process as in claim 1 wherein the casting the plastisol formulation comprises one of i) three roll coating, ii) knife over roll coating, and iii) slot coating.

10. A one stage process for the manufacture of a plastisol foam tape laminate comprising:
    providing a continuous liner;
    forming a release layer along the length of one side of the liner;
    depositing an adhesive onto the release layer;
    casting a foamable liquid plastisol formulation onto the adhesive, wherein the adhesive is dried prior to casting the liquid plastisol, formulation;
    fusing and expanding the foamable plastisol formulation to form a plastisol foam on the adhesive; and
    winding the foam tape laminate onto rolls.

11. The process of claim 10 wherein the liner comprises a paper liner of about 40 to about 100 pounds weight.

12. The process of claim 11 wherein the paper liner is clay coated.

13. The process of claim 10 wherein the release layer comprises a silicone release composition.

14. The process of claim 13 wherein the release layer comprises a polydimethyl siloxane composition.

15. The process of claim 10 including depositing the adhesive in a pattern.

16. The process of claim 10 wherein the adhesive comprises a pressure sensitive adhesive.

17. The process as in claim 10 wherein the adhesive comprises an acrylic adhesive.

18. The process of claim 10 wherein the adhesive contains a cross-linking agent.

19. The process of claim 10 wherein the adhesive comprises a vinyl pyrrolidone polymer and a cross-linking agent.

20. The process of claim 10 wherein the adhesive comprises an acrylic polyvinyl ester.

21. The process as in claim 10 wherein the plastisol comprises polyvinyl chloride plasticizer and a blowing agent.

22. The process as in claim 21 wherein the plastisol additionally comprises at least one of a polyvinyl chloride blending resin, an activator, a stabilizer, a viscosity depressant, a defoamer, a solvent, a filler and a pigment.

23. The process as in claim 10 wherein the casting the plastisol formulation comprises one of i) three roll coating, ii) knife over roll coating, and iii) slot coating.

24. The process as in claim 10 wherein the plastisol formulation is expanded by heating the formulation at about 300° to about 400° F.

25. The process as in claim 10 further including cutting the foam tape laminate substantially parallel to its long axis to a selected width.

26. A foam tape laminate produced by the process of claim 1.

27. A foam tape laminate produced by the process of claim 10.

28. A skin bandage produced by the process of claim 10.

29. A process for the manufacture of a tape comprising:
    providing a continuous liner having a release layer;
    depositing an adhesive onto the release layer;
    casting a liquid plastisol formulation onto the adhesive; and,
    fusing the plastisol formulation to form a thermoplastic film layer on the adhesive.

30. The process as in claim 29 including applying the release layer to the liner prior to the depositing of the adhesive.

31. The process as in claim 29 wherein the adhesive is dried prior to casting the liquid plastisol formulation.

32. The process as in claim 29 wherein the plastisol comprises polyvinyl chloride, and a plasticizer.

33. The process as in claim 32 wherein the plastisol additionally comprises at least one of a polyvinyl chloride blending resin, an activator, a stabilizer, a viscosity depressant, a defoamer, a solvent, a filler and a pigment.

34. The process as in claim 32 wherein the plastisol formulation is fused by heating the formulation at about 300° to about 400° F.

35. The process as in claim 29 further including cutting the tape substantially parallel to its long axis to a selected width.

36. The process as in claim 29 further including winding the tape onto rolls.

37. The process as in claim 29 wherein the adhesive comprises an acrylic adhesive.

38. The process as in claim 29 wherein the casting the plastisol formulation comprises one of i) three roll coating, ii) knife over roll coating, and iii) slot coating.

39. A one stage process for the manufacture of a tape laminate comprising:

providing a continuous liner;

forming a release layer along the length of one side of the liner;

depositing an adhesive onto the release layer;

casting a liquid plastisol formulation onto the adhesive;

fusing the plastisol formulation to form a thermoplastic film layer on the adhesive; and, winding the resulting tape laminate onto rolls.

40. The process of claim 39 wherein the liner comprises a paper liner of about 40 to about 100 pounds weight.

41. The process of claim 40 wherein the paper liner is clay coated.

42. The process of claim 39 wherein the release layer comprises a silicone release composition.

43. The process of claim 42 wherein the release layer comprises a polydimethyl siloxane composition.

44. The process of claim 39 including depositing the adhesive in a pattern.

45. The process as in claim 39 wherein the adhesive is dried prior to casting the liquid plastisol formulation.

46. The process of claim 39 wherein the adhesive comprises a pressure sensitive adhesive.

47. The process as in claim 39 wherein the adhesive comprises an acrylic adhesive.

48. The process of claim 39 wherein the adhesive contains a cross-inking agent.

49. The process as in claim 39 wherein the adhesive comprises a vinyl pyrrolidone polymer and a cross-linking agent.

50. The process of claim 39 wherein the adhesive comprises an acrylic polyvinyl ester.

51. The process as in claim 39 wherein the plastisol comprises polyvinyl chloride and a plasticizer.

52. The process as in claim 51 wherein the plastisol additionally comprises at least one of a polyvinyl chloride blending resin, an activator, a stabilizer, a viscosity depressant, a defoamer, a solvent, a filler and a pigment.

53. The process as in claim 39 wherein the casting the plastisol formulation comprises one of i) three roll coating, ii) knife over roll coating, and iii) slot coating.

54. The process as in claim 39 wherein the plastisol formulation is fused by heating the formulation at about 300° to about 400° F.

55. The process as in claim 39 further including cutting the foam tape laminate substantially parallel to its long axis to a selected width.

56. A film tape laminate produced by the process of claim 29.

57. A film tape laminate produced by the process of claim 39.

58. A skin bandage produced by the process of claim 39.

59. The process as in claim 1, including depositing the foamable liquid plastisol onto an adhesive/release/liner laminate in a stage separate from the depositing of the adhesive.

60. The process as in claim 29, including depositing the liquid plastisol onto an adhesive/release/liner laminate in a stage separate from the depositing of the adhesive.

* * * * *